United States Patent
Izmailov

(10) Patent No.: US 6,397,150 B1
(45) Date of Patent: May 28, 2002

(54) METHOD AND APPARATUS FOR SEQUENCING OF DNA USING AN INTERNAL CALIBRANT

(75) Inventor: Alexandre M. Izmailov, Etobicoke (CA)

(73) Assignee: Visible Genetics Inc., Toronto (CA)

( * ) Notice: Subject to any disclaimer, the term of this patent is extended or adjusted under 35 U.S.C. 154(b) by 0 days.

(21) Appl. No.: 09/628,736

(22) Filed: Jul. 27, 2000

(51) Int. Cl.[7] ............................. C12Q 1/68; G06F 19/00
(52) U.S. Cl. ............................................. 702/20; 435/6
(58) Field of Search ............................. 435/6; 364/497; 702/17, 20

(56) References Cited

U.S. PATENT DOCUMENTS

| | | | |
|---|---|---|---|
| 4,849,513 A | 7/1989 | Smith et al. | |
| 4,855,225 A | 8/1989 | Fung et al. | |
| 5,096,557 A | * 3/1992 | Simons | 204/182.8 |
| 5,118,800 A | 6/1992 | Smith et al. | |
| 5,124,247 A | 6/1992 | Ansorge | |
| 5,171,534 A | 12/1992 | Smith et al. | |
| 5,213,673 A | 5/1993 | Fuimiya et al. | |
| 5,268,486 A | 12/1993 | Waggoner et al. | |
| 5,365,455 A | 11/1994 | Tibbetts et al. | |
| 5,608,063 A | 3/1997 | Hobbs, Jr. et al. | |
| 5,614,386 A | 3/1997 | Metzker et al. | |
| 5,666,435 A | 9/1997 | Burgi et al. | 328/129 |
| 5,834,189 A | 11/1998 | Stevens et al. | |
| 5,916,747 A | * 6/1999 | Gilchrist et al. | 435/6 |
| 5,981,186 A | 11/1999 | Gabe et al. | |
| 6,013,444 A | * 1/2000 | Dau et al. | 435/6 |
| 6,027,709 A | 2/2000 | Little et al. | |
| 6,068,737 A | 5/2000 | DeChamorro et al. | |

FOREIGN PATENT DOCUMENTS

| | | |
|---|---|---|
| WO | WO 95/11961 | 5/1995 |
| WO | WO 97/04184 | 10/1997 |
| WO | WO 98/41650 | 9/1998 |
| WO | WO 00/68410 | 11/2000 |

OTHER PUBLICATIONS

Michael C. Giddings, et al., An adaptive, object oriented strategy for base calling in DNA sequence analysis; Nucleic Acids Research, 1993, vol. 21, No. 19.

James B. Golden, III, et al., Pattern Recognition for Automated DNA Sequencing: I. On–line Signal Conditioning and Feature Extraction for Basecalling; Dept. of Mechanical Engineering, Dept. of Microbiology and Immunology, Vanderbilt University Schools of Medicine and Engineering, Nashville, TN 37232–2363.

(List continued on next page.)

Primary Examiner—Ardin H. Marschel
(74) Attorney, Agent, or Firm—Oppedahl & Larson LLP

(57) ABSTRACT

For evaluation of a target DNA sequence, a sample mixture is prepared containing one or more sets of sequencing polynucleotide fragments, each set containing fragments having lengths indicative of the positions of at least one base within the target DNA sequence. These sequencing fragment sets are each labeled with a different type of label (for example fluorescent labels). The sample mixture also includes a set of calibrant polynucleotide fragments having a plurality of known fragment lengths. The calibrant polynucleotide fragments are labeled with a spectroscopically-distinguishable calibrant label. The sample mixture is then electrophoretically separated to separate the polynucleotide fragments as a function of fragment length. Real-time detection is used to detect the label(s) on the set(s) of sequencing fragments and the calibrant label as they migrate in a common lane of the separation medium to produce a sequencing data trace and a calibrant data trace. The calibrant peaks are then used to define a set of coefficients for linearizing the sequencing data trace from each lane to a common corrected time scale in which the peaks from each lane are evenly spaced. The linearized sequencing data traces are then aligned by assigning base position numbers to each peak in the sequencing data traces, and these aligned traces are used for base calling.

18 Claims, 9 Drawing Sheets

OTHER PUBLICATIONS

Lance B. Koutny, et al., Automated Image Analysis for Distortion Compensation in Sequencing Gel Electrophoresis; 1369 Applied Spectroscopy 46(1992 Jan., No. 1, Frederick, MD, US.

Keith Kretz, et al., Cycle Sequencing, PCR Methods and Applications S107–S1112., Manual Supplement.

Michael A. Reeve et al., A novel thermostable polymerase for DNA sequencing; Nature, vol. 376, Aug. 31, 1995.

Gualberto Ruano, et al., Coupled amplification and sequencing of genomich DNA; Proc. Natl. Acad. Sci. USA, vol. 88, pp. 2815–281, Apr. 1991, Genetics.

C. Tibbetts, et al., Neural Networks for Automated Basecalling of Gel–based DNA Sequencing Ladders; Dept. of Microbiology and immunology, Dept. of Mechanical Engineering, Vanderbilt University Schools of Medicine and Engineering, Nashville, TN 37232–2363, USA.

Stefan Wiemann, et al., Simultaneous On–Line DNA Sequencing on Both Strands with Two Fluorescent Dyes; Analytical Biochemistry 224, 117–121 (1995).

* cited by examiner

# METHOD AND APPARATUS FOR SEQUENCING OF DNA USING AN INTERNAL CALIBRANT

BACKGROUND OF THE INVENTION

This application relates to a method and apparatus for sequencing of DNA. The method of the invention makes use of an internal calibrant track which is co-electrophoresed with DNA sequencing fragments to facilitate linearization and alignment of the tracks for accurate base calling.

DNA sequencing is becoming an increasingly important diagnostic tool, and also forms an important component of research efforts such as the Human Genome Project. The most common sequencing procedures used today are based on the primer extension or "Sanger" methodology. In the Sanger DNA sequencing method, a 5'-end-labeled oligodeoxynucleotide primer is bound sequence-specifically to a target DNA template which is to be sequenced. The primer is extended by a DNA polymerase enzyme, via incorporation of dNTPs. A chain-terminating dideoxy-NTP of one particular base type (A, C, G, T) is added to the reaction, to effect a termination of DNA chains at random positions along the sequence. The nested series of DNA fragments produced in this reaction is loaded on one lane of a thin denaturing polyacrylamide gel, and the bands are electrophoretically resolved, to produce a series of bands in the profile of that lane. A set of four reactions (with chain termination occurring via ddA, ddC, ddG, ddT incorporation) is required for explicit determination of the positions of all four bases in the sequence, and typically is run on four adjacent lanes of a sequencing gel.

Data traces are collected indicating the peak positions in each of the four lanes of a gel. In an ideal system, these four data traces could simply be placed one over another and the sequence could be read. This reading process is called "base calling." In practice, however, the data traces are not ideal because of a variety of factors including mobility differences between lanes and changes in resolution which occur as the size the fragments increases. Prior to the development of automated sequencing apparatus, the data traces were generally aligned prior to base calling by eye, i.e., a skilled technician looked at the traces and shifted the positions of the traces based on accumulated experience. One of the challenges of automated DNA sequencing is the proper alignment of the data traces using computer processing rather than human analysis.

Various approaches have been taken to the need for accurate trace alignment which is an essential prerequisite to accurate base calling. One approach is the use of a multi-dye sequencer, in which the traces for all four bases are obtained from a single lane of a gel. (See, for example, U.S. Pat. No. 5,171,534) This reduces many of the sources of variability, but requires the utilization of four different label types, and may involve an increase in the complexity of the detection apparatus. Another approach is described in commonly assigned U.S. Pat. No. 5,916,747. The present application provides another approach to the solution of this problem.

SUMMARY OF THE INVENTION

The present invention provides a method for evaluation of a target DNA sequence. The first step in the method is the preparation of a sample mixture containing one or more sets of sequencing polynucleotide fragments, each set containing fragments having lengths indicative of the positions of at least one base within the target DNA sequence. These sequencing fragment sets are each labeled with a different type of spectroscopically detectable label (for example a fluorescent label). The sample mixture also includes a set of calibrant polynucleotide fragments having a plurality of known fragment lengths. The calibrant polynucleotide fragments are labeled with a calibrant label which is spectroscopically-distinguishable from the label(s) on the set(s) of sequencing fragments. The sample mixture is then electrophoretically separated to separate the polynucleotide fragments as a function of fragment length in a separation medium such as a polyacrylamide electrophoresis gel. Real-time detection is used to detect the label(s) on the set(s) of sequencing fragments and the calibrant label as they migrate in a common lane of the separation medium to produce a sequencing data trace and a calibrant data trace. The calibrant peaks are then used to define a set of coefficients for linearizing the sequencing data trace from each lane to a common corrected time scale in which the peaks from each lane are evenly spaced. The linearized sequencing data traces are then aligned by assigning base position numbers to each peak in the sequencing data traces, and these aligned traces are used for base calling.

The method of the invention is suitably employed for sample mixtures which contain two sets of sequencing polynucleotide fragments representing the positions of two type of bases in the target DNA sequence. In this case, the two sets of sequencing polynucleotide fragments are each labeled with a different label, the first label and a second label, which are spectroscopically distinguishable from each other and from the calibrant label.

The method of the invention can be practiced using a sequencing apparatus having a detection system adapted for detection of two or more spectroscopically-distinguishable label types. The apparatus of the invention differs from prior art devices, however, since one of the detected labels is the calibrant data trace, not a sequencing data trace. This means that the data processing which is performed on the data traces is different.

DETAILED DESCRIPTION OF THE INVENTION

Figure 1:
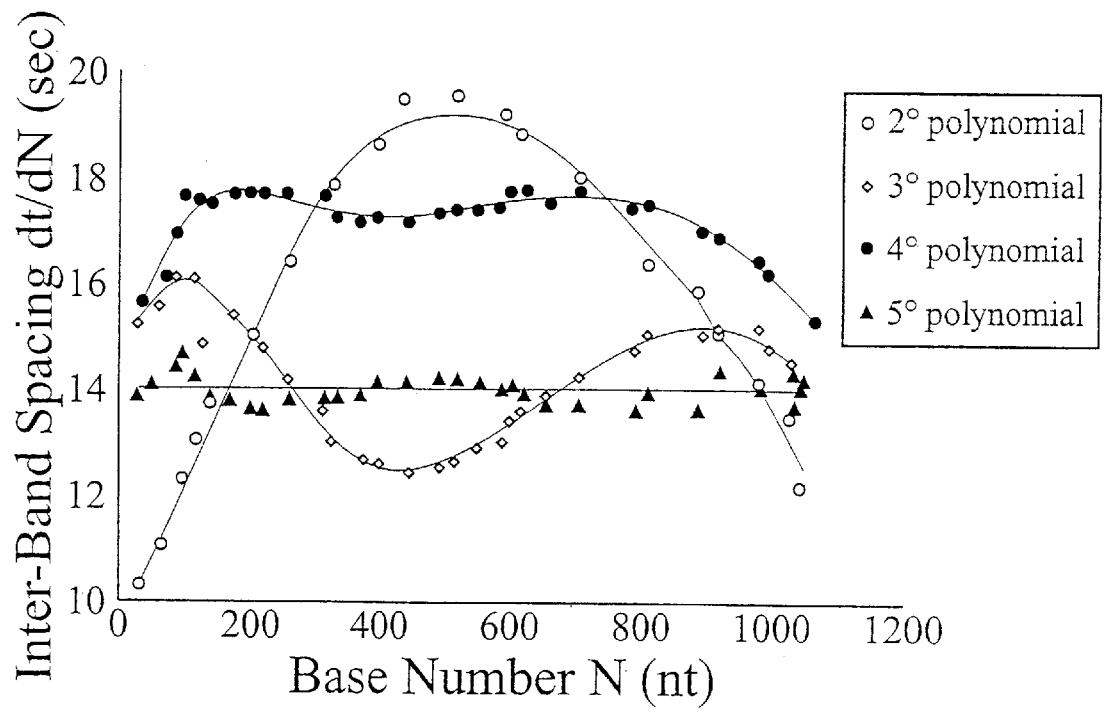
FIG. 1 illustrates the effect of polynomial degree on the linearization step of the invention.

The present invention relates to a new method for the alignment of data traces generated by automated DNA sequencing instruments utilizing a Sanger-type methodology in which fragments indicative of the positions of bases within a target DNA sequence are analyzed. Such alignment is used to compensate for variations in migration time that can occur as a result of variations in the separation medium, localized heating, and other experimental variables, and to correct for the gradual changes in peak spacing which occur over the course of a separation. As a result of these and other factors, in current, state-of-the-art, automated DNA sequencing, the upper limit for reading length falls around 800–900 nt, although longer reads are occasionally reported. This represents a substantial limitation on the ability to perform some diagnostic analysis in a cost-effective manner where the region of interest spans more that 800–900 nt. The present invention allows sequencing of target polynucleotide regions in excess of 1000 nt, while maintaining the accuracy of the final base call at levels in excess of 97%.

As used in the specification and claims of this application, the term "linearization" refers to the process of mathematically modifying experimental sequencing data traces to achieve the even peak spacing which would be anticipated in an ideal system. In a linearized data trace, peaks associated with adjacent bases are separated by a standard distance or time, and peaks associated with non-adjacent bases are separated by an integral multiple of this standard distance or time.

As used in the specification and claims of this application, the term "alignment" refers to the positioning of data traces relative to one another such that the peaks corresponding to the same base number are disposed in all traces at the same time, or peaks adjacent to a given peak are shifted from this peak at a distance equal to a standard distance or time to provide a correct base calling result, i.e., a result corresponding to the actual sequence of the target nucleic acid. Alignment can be done with different representations of the data traces, however. Thus, while alignment is perhaps easier to understand by consideration of graphical depictions of the data traces in which peaks representing each base are shown, other representations are useful. For example, the graphical data trace can be converted into a peak list (for example a listing of detection times after the start of electrophoresis). In the alignment procedure, each member of this peak list is associated with a unique sequencing position number indicating the position of the base represented by the peak within the sequence, and the peak lists are combined to place the peaks in order based on the sequencing position numbers.

As used in the specification and claims of this application the terms may refer to a single wavelength (for example when referring to a monochromatic light source) or to a spectral band. In the latter case, it will be appreciated by persons skilled in the art that the excitation and emission observed for fluorescent labels in a gel medium are not single wavelength peaks, but are rather broad bands. Thus, when the "wavelength" of an emission is referred to it does not refer to a specific single wavelength, but rather to light within this spectral band.

In the method of the invention, one or more sets of sequencing polynucleotide fragments are combined with a set of calibrant polynucleotide fragments in a sample mixture which is loaded onto a lane of a separation medium such as a polyacrylamide electrophoresis gel. As used in the specification and claims of this application, the term "set of sequencing polynucleotide fragments" refers to a collection of polynucleotide fragments whose lengths reflect the position of one type of base within a target DNA sequence. When more than one set of sequencing polynucleotide fragment is included in a sample mixture, the sets may be derived from various different sources. In one embodiment, the sets of sequencing polynucleotide fragments reflect the positions of two or more different bases in the same target DNA sequence (for example A and C sets). As used in the specification and claims of this application, sequencing fragments sets of this type are referred to as "related", since they may be combined to produce a combined data set for base calling of the target sequence. In another embodiment, the sets of sequencing polynucleotide fragments reflect the positions of the same base in the forward and reverse strands of a target DNA sequence. In yet a third embodiment, the sets of sequencing polynucleotide fragments each reflect the positions of a base (which may be the same or different between sets) in different target DNA sequences. The latter might be used when performing the same analysis on multiple samples, for example when the A fragments for all of the samples are pooled in one sample mixture. (See WO 97/40184 for an example methodology of this type).

In addition to one or more sets of sequencing polynucleotide fragments, the sample mixture loaded onto the gel when practicing the method of the invention also includes a set of calibrant polynucleotide fragments. The specific attributes of the calibrant polynucleotide fragment set are discussed in greater detail below. In general, however, the set of calibrant nucleotide fragments includes fragments of a plurality of different and known lengths.

Each set of sequencing polynucleotide fragments and the set of calibrant polynucleotide fragments combined in a sample mixture are labeled with a detectable label. Preferred labels are fluorescent labels which can be readily detected in a real-time environment as the labeled fragments migrate through a separation matrix. The label used with each set of polynucleotides should be spectroscopically distinguishable from the labels used for other sets. As used herein, the term "spectroscopically distinguishable" refers to labels which can be distinguished from one another as a result of differences in absorption spectra, or, for fluorescent labels, excitation spectra, emission spectra or both. Thus, two or more fluorescent labels may be used which absorb light of the same excitation wavelength, provided that the resulting emission is of sufficiently different wavelength that it can be separated and/or distinguished using optical components such as filters, spectrophotometers or optical multichannel analyzers. Similarly, two or more fluorescent labels may be used which emit light of the same emission wavelength, provided that the emission occurs when light of different wavelength is used as the excitation source. In addition, as is well known in the art, the labels should be selected in combinations such that the different labels employed do not themselves impart disparate differences in electrophoretic mobility to the labeled polynucleotide fragments. As illustrated below, specific combinations of labels which can be employed in the method of the invention are cyanine dye labels known in the art and sold under the tradenames CY5, CY5.5 and CY7. Other combinations of labels which are responsive to different excitation wavelengths, or provide different emission wavelengths can also be used. Examples of such dyes are found in U.S. Pat. Nos. 6,068,737, 6,027,709, 5,614,386, 5,268,486, 5,118,800, 4,849,513, and 4,855,225.

To assess the characteristics which are required for the calibrant polynucleotide fragment set, an M13mp18 single-stranded DNA template was used as the target DNA sequence. Three sets of fragments were prepared by cycle sequencing methods. The sets were labeled with CY5, CY5.5 or CY7 cyanine dyes. Eight sample mixtures were prepared containing CY5-labeled sequencing fragments sets (A, C, G and T sets) and CY5.5-labeled sequencing fragment sets (A, C, G and T sets). Each sample mixture also included a CY7-labeled set of calibrant polynucleotide fragments. For assessment of the required characteristics of the calibrant polynucleotide fragment set, the fragments used were generated from M13 in the same manner as the sequencing fragment sets. As will be explained below, however, the calibrant polynucleotide fragment set may be derived from a different source or may be a mixture of synthetic polynucleotides.

The sample mixtures were loaded into adjacent lanes of a Visible Genetics MICROCEL™ electrophoresis cassette filled with polyacrylamide gel. Once loaded, a high voltage is applied to the gel in the cassette from a built-in stabilized power supply in the Visible Genetics LONG READ TOWER™ automated sequencer. Typically a voltage of 2500–2800 V is dropped over an interelectrode distance of 28 cm. Data traces were collected using the optical system of the sequencer at a sampling interval of 0.5 sec. Thus, 8 sequencing data traces (one for each sample mixture/lane) and 8 calibrant data traces (one for each sample mixture/lane) were obtained. These data traces were used to evaluate the characteristics required for an effective calibrant polynucleotide fragment set and for effective linearization and alignment using the resulting calibrant data trace.

The process of the invention occurs in several steps. The first step of is the identification of peaks in the calibrant data trace. Automated peak identification procedures are known in the art, and the type of procedure used is not critical as long as it identifies peaks with reasonable accuracy (>95%). Various peak identification procedures are known in the art (for example from U.S. Pat. No. 5,916,747). Peak identification results in a calibrant data set, consisting of a list of peak times and the corresponding size of the fragment which produced them. A separate calibrant data set is generated for each lane, i, of the gel, and can be represented by the mathematical expression $\{N, t_{iN}\}$, where N is the peak number and $t_{iN}$ is the experimental migration of the peak. The generation of this data set is easily accomplished once the peaks are identified since the sizes of the fragments in the calibrant polynucleotide fragment set are known.

The calibrant data set is then fit to a polynomial function, $t_{iN}^*$, for example by a least squares procedure. The function $t_{iN}^*$ has the form:

$$t_{iN}^* = a_{i0} + a_{i1}N + a_{i2}N^2 + \ldots a_{ik}N^k. \quad (1)$$

The degree of the polynomial, k, may be an input parameter of the fitting program or may be fixed. The fitting procedure generates a set of coefficients, $\{a_{ik}\}$, for each gel lane, i. In the least squares fitting procedure, the value of these coefficients are found by minimizing the sum-of-squares:

$$SS = \sum_N (t_{iN} - t_{iN}^*)^2 \quad (2)$$

wherein the sum is taken over all calibration bands in lane i. There is an almost-linear relationship between $t_{iN}$ and N over the useful range of DNA chain lengths. Thus, the higher coefficients in equation (1), especially above the fourth order are relatively small. Nevertheless, it was found that linearization is best achieved using a fitting program where the polynomial is a fifth order or greater polynomial (i.e., $k \geq 5$).

Once the set of polynomial coefficients is developed for the calibrant data trace for lane i, a corrected time scale is defined for each peak in that lane according to the formula:

$$T_{iN} = C_i[a_{i0} + a_{i1}t_{iN}N + a_{i2}t_{iN}N^2 + \ldots + a_{ik}t_{iN}N^k] \quad (3)$$

where $T_{iN}$ is the corrected time value for peak N in the calibrant data trace, $t_{iN}$ is the experimentally measured migration time for this peak, and $C_i$ is a scaling factor. This transformation is applied to data sets derived from the sequencing data traces to produce linearized sequencing data sets, in a corrected time domain in which the peaks have even spacing over the length of the run.

In the method of the invention, each gel lane i has a scaling factor $C_i$ which is determined for that specific lane. This means that all of the scaling factors may be different, although it will be appreciated that in cases where the performance of a gel approaches ideal the scaling factors may be the same or very similar. The set $\{C_i\}$ of values of the scaling factors is chosen to equalize the spacing between consecutive peaks in the corrected time domain ($dT_{iN}/dN$) across all lanes of the gel. The value of $dT_{iN}/dN$ equals the "grand canonical average" for base pair spacing in real time (i.e., the average across all peaks in each gel lane, and across all gel lanes). A gel lane is uniformly compressed by setting $C_i>1$, and it is uniformly stretched by setting $C_i>1$. A set of coefficients $\{C_i\}$ can therefore be defined such that all lanes of the gel have the same total run time in the corrected time domain.

While it is straightforward to create the $\{N, t_{iN}\}$ data set from the calibrant data trace because the lengths of the fragments (i.e, the values of N) are known, the same is not true for the sequencing data traces because the base number associated with any given peak is not known, and is in fact that which is to be determined. Thus, what is required is a resampling of the experimental sequencing data traces using a sampling protocol defined by the fit of the calibrant data set. In this resampling, the sequencing is looked at again at equally-spaced intervals in the corrected time-domain by quadratic interpolation to produce the final, linearized data sets which will be aligned for base calling. This procedure is done separately for each gel lane, because the corrected time scale may be different for each lane.

To understand the resampling procedure, one can look at equation (3). After fitting the calibrant data trace, all of the parameters in the equation are known. It is therefore possible to calculate the real time $t_{iN}$ at which any given peak N should appear. By looking at the raw sequencing data trace, or the raw peak list at each such time to see if a peak is present, one can assign peak numbers to each peak in the sequencing data list. An additional step which may be part of a resampling procedure involves the resampling of the data in the corrected time domain so that the data points which make up the data trace are now disposed at an equal spacing. This can be accomplished by quadratic interpolation from the values of the original data points. This step is not required, but may be a convenience since many base calling programs are designed to receive evenly-spaced data points.

As noted above, the degree k of the polynomial is a parameter which can be adjusted to optimize the data linearization process. FIG. 1 illustrates how the choice of polynomial degree affects the linearization. A set of 10 peaks, evenly spaced between 40 nt and 1,056 nt on an M13 T sequencing run were selected as a model calibrant data trace, and were transformed in the time domain according to equations 1–3, and with k values of 2, 3, 4 or 5. Neither the $2^{nd}$ nor the $3^{rd}$ degree polynomials produced acceptable linearization. Increasing the polynomial to $4^{th}$ degree produced a significant improvement in linearity. However, for short nucleotide fragments (<100 nt) and long fragments (>900 nt), the experimental points still deviated significantly from a straight line. Linearization with a $5^{th}$ degree polynomial produced the best result. Thus, in practicing the method of the invention, the calibrant data trace should in most cases be fit to at least a $4^{th}$ degree polynomial, and preferably at least a $5^{th}$ degree polynomial. An exception to this is discussed below.

It should be noted that with a $5^{th}$ degree polynomial, the maximum deviation from linearity is less than 0.5 seconds across the entire 40–1056 nt window. This is close to the theoretical limit, because the data sampling period is 0.5 seconds in this experiment. Accordingly, with this sampling rate, further increases in polynomial degree would not be expected to produce any additional improvement in linearization. However, higher order polynomials might be indicated if the sampling interval were significantly shortened.

Figure 2:
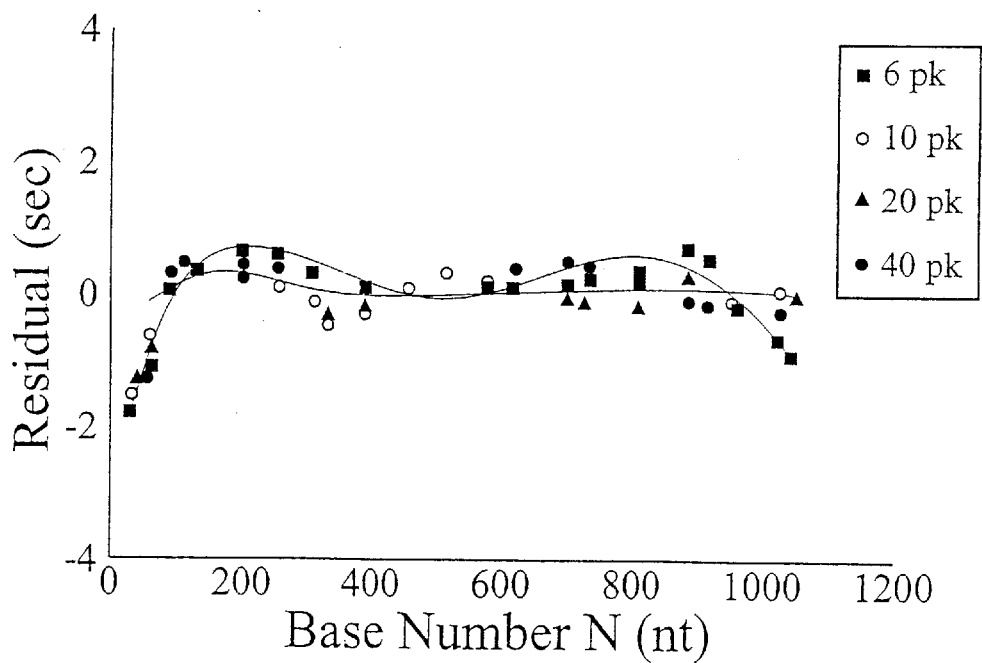
FIG. 2 shows the effect of varying the number of calibrant peaks on the residual after linearization.

A second important parameter in the linearization process is the number of peaks in the calibrant data set used in the polynomial fit. Since the fit produces a set of polynomial coefficient $\{a_{ik}\}$ with k elements, for the fit to be determinate, at least k+1 calibrant peaks must be employed. A separate calibrant peak is not required for the scaling factor $C_i$, since this factor is not independent of the set of polynomial coefficients. Using the M13 T sequencing trace as a calibrant data trace allowed the testing of a 5 $^{th}$ degree polynomial using 6, 10, 20 or 40 peaks selected from among the M13 T peaks in the data trace at substantially even spacing over the region sequenced. The quality of the least-square fit can be characterized by a "residual" which can be defined as the difference between the average peak spacing and the observed peak spacing between two adjacent bases after linearization. A perfect linearization would yield a residual of 0, because the observed peak spacing would always be equal to the average peak spacing. FIG. 2 shows the residual as a function of base number when 6, 10, 20 and 40 calibrant peaks are included in the calibrant data set. As shown, 6 calibrant peaks (the minimum for making the coefficients determinate) are sufficient to provide good linearization over the~1000 nt sequence. The maximum residual did not exceed 2 sec, which corresponds to less than 0.2 nt. However, there is a slightly higher deviation from linearity at the beginning and end of the fitting window. This can be substantially reduced by increasing the number of calibrant peaks to 10. No additional improvement was observed by increasing the number of calibrant peaks to 20 or 40. Thus, while the calibrant fragment set may include any convenient higher number of fragment sizes (depending on the method of generation), it should include at least 6 fragments and preferably at least 10 fragments when using a $5^{th}$ degree polynomial. If using a 4th degree polynomial, the minimum number of fragments would be 5.

Figure 3A:
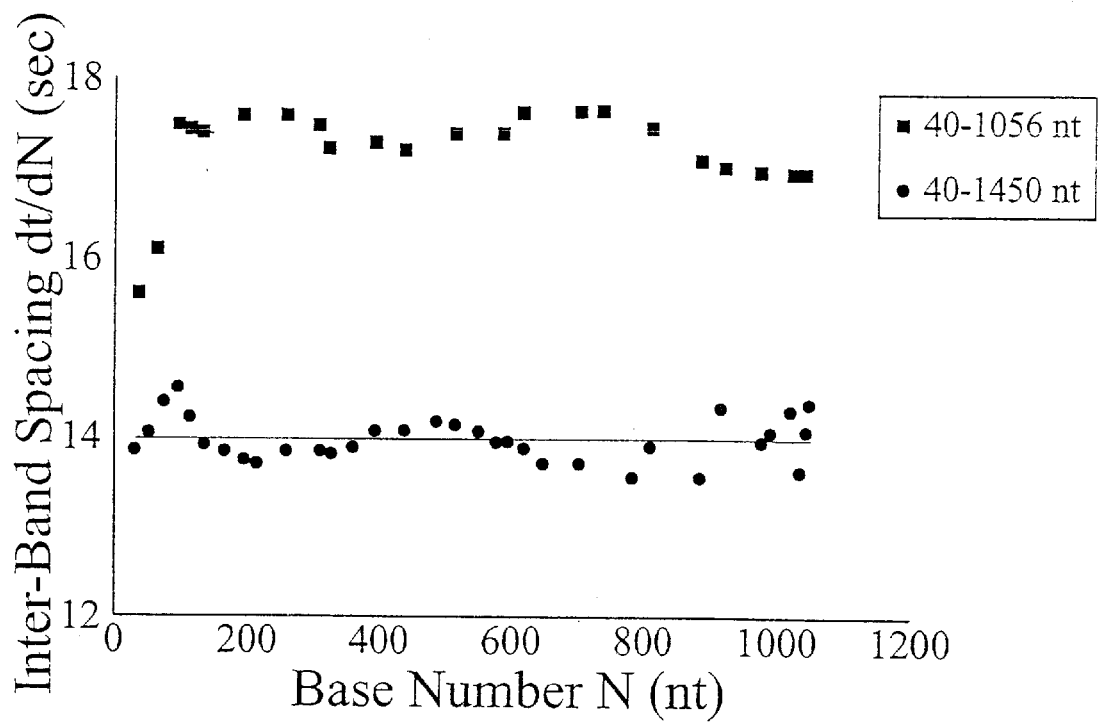
FIG. 3A shows a plot of internucleotide spacing as a function of base number.
Figure 3B:
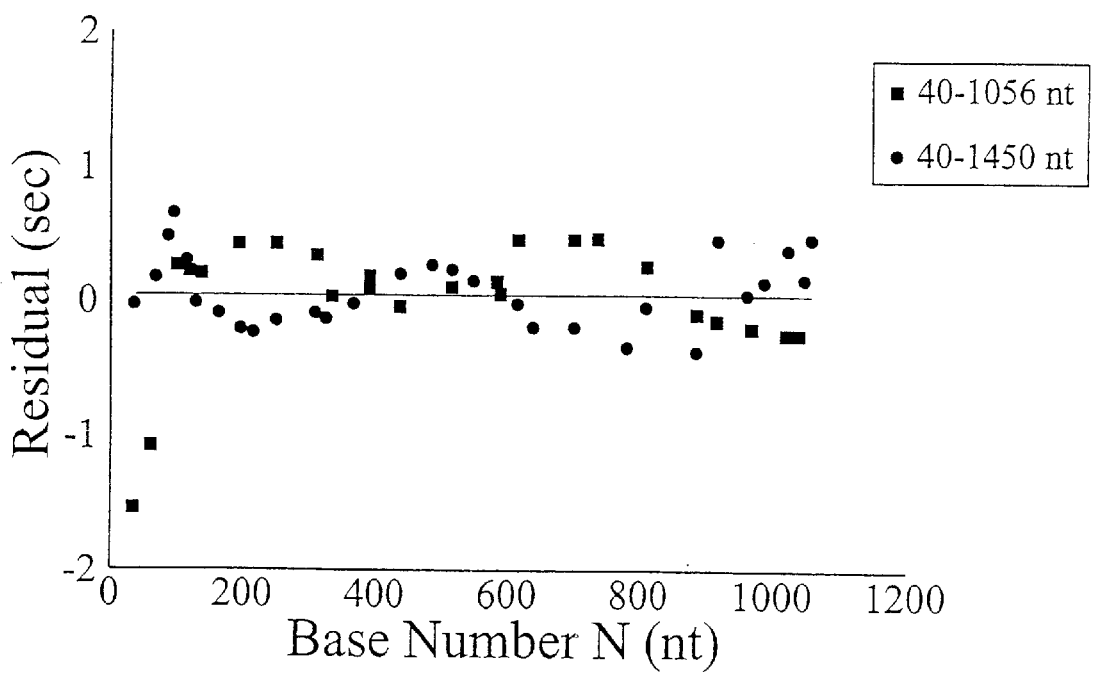
FIG. 3B shows a plot of residuals as a function of base number.

Another parameter which can be varied in practicing the method of the invention is the placement of the "fitting window", i.e., the range of sizes spanned by the fragments in the calibrant fragment sets. To investigate the importance of this parameter, data was linearized using a $5^{th}$ degree polynomial and 40 calibrant peaks. In the first case, the calibrant peaks were approximately evenly spaced peaks taken over the 40–1056 nt window. In the second case, the calibrant peaks were approximately evenly spaced peaks taken over a wider window spanning nucleotides 40–1450. FIG. 3A shows a plot of internucleotide spacing as a function of base number. As can be seen, the average spacing is less when the calibrant points are taken across a larger fitting window. This arises because the resolution (and hence the actual spacing between adjacent peaks) is declining in the added portion of the window and this is reflected in the scaling factor. However, when one considers the residuals (FIG. 3B) it is apparent that either fitting window provides good linearization with maximum residuals on the order of 1.5–2 sec, which corresponds to <0.1 nt for the narrow window, and <0.5 sec, which corresponds to <0.03 nt for the wider window. Thus, the selection of fitting window does not appear to be critical.

A corollary which may be drawn from these results relates to the spacing of the calibrant peaks. While the calibrant peaks used in the examples described in this application were selected to provide approximately equal spacing over the length of the window, the use of evenly spaced peaks is not a requirement. Rather, the calibrant peaks need only be representative of the of the data trace so that there is not too much freedom in the selection of a polynomial that fits the data (i.e, multiple different solutions of substantially equal fit quality). In general, this means that the distance between adjacent calibrant points should be less than the characteristic size of peculiarities in the curve under consideration, but pairs of calibrant peaks may be located at a greater or less er spacing provided that the calibrant provided that the overall data set is representative.

Having completed the linearization of the data sets, what one has (in the case of a four base analysis with text data sets) is four lists of base position numbers, an A list, a C list, a G list and a T list. These lists of base position numbers can be used directly for base calling. A graphical display of the aligned traces in the corrected time domain may also be provided to allow visual inspection of the quality of the alignment by a human operator.

Figure 4A:
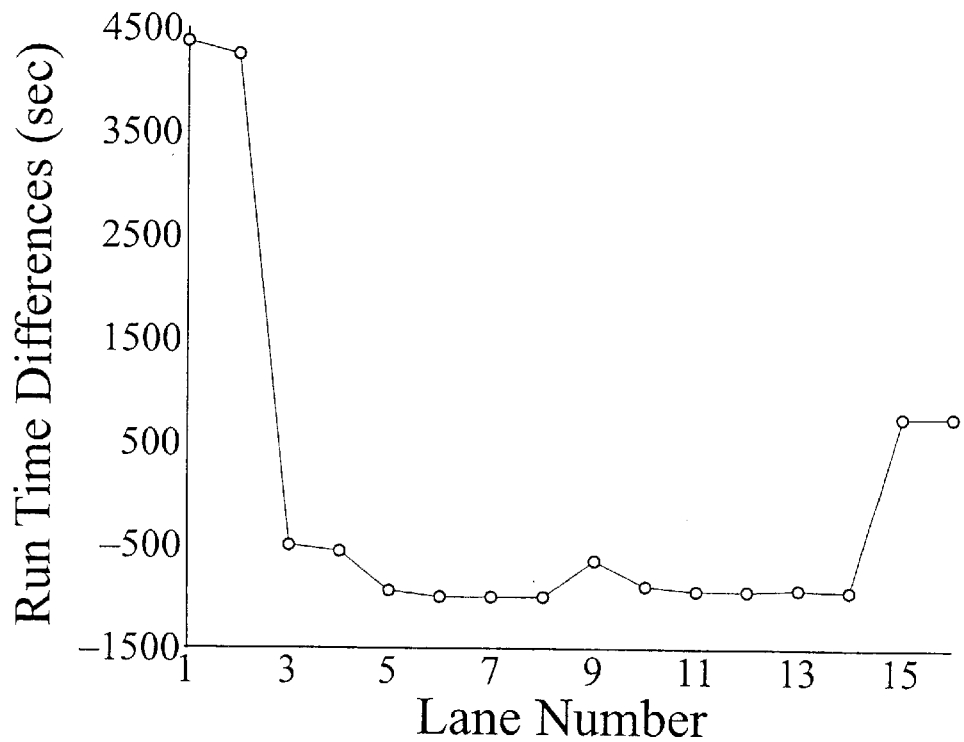
FIGS. 4A and B show total run times for replicate samples in different lanes of a gel before and after linearization in accordance with the invention.
Figure 4B:
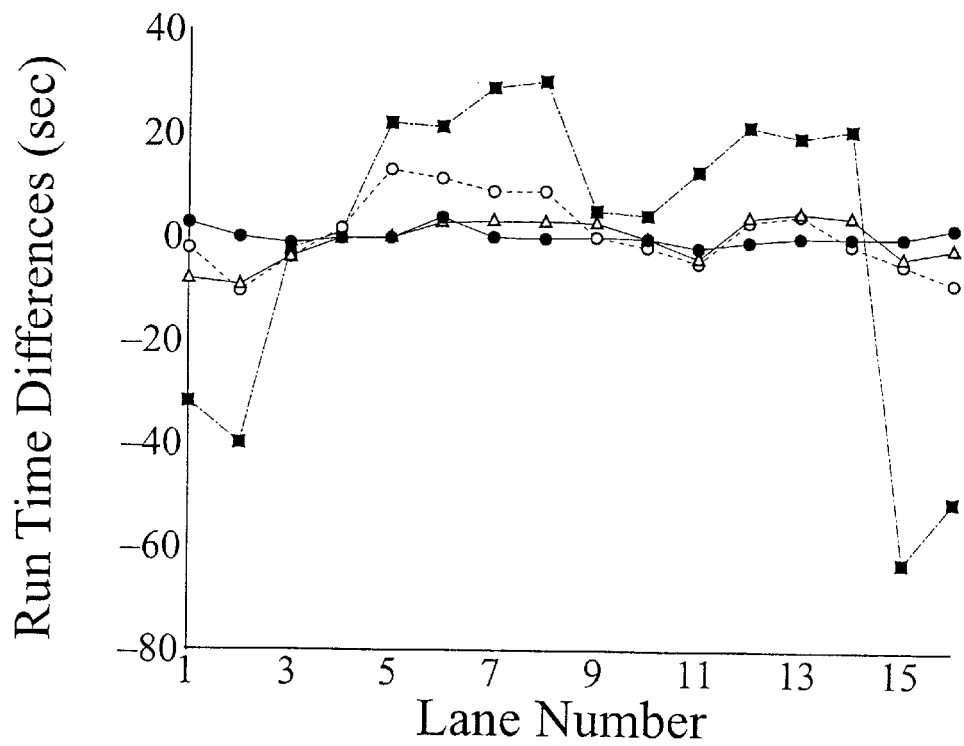

The linearization and alignment procedure described above corrects for both systematic and random distortions of electrophoretic velocity which may occur during an electrophoresis run. Systematic variations are those which result from changing conditions along some direction vector within the gel. While it is not necessary to know the cause of a variation to use the present invention, it is known that substantial systematic variations can arise as a result of temperature gradients within the gel. Random and in some cases systematic variation may arise as a result of inhomogeneities within the gel, for example stemming from inclusion of small bubbles or impurities. These variations in run time can be very large. For example in replicate runs of sequencing fragments for a 922 nt on a 25 cm MICROCEL™ gel, differences in total run time between lanes 1 and 3 in excess of 90 minutes, 25% of the average total run time, were observed as reflected in FIG. 4A. FIG. 4B shows the post-alignment run times of replicate DNA fragments (922 nt long) in the 16 individual lanes of a 25 cm MICROCEL™ gel. Linearization and alignment were conducted with a 2nd degree polynomial (3 alignment points at positions 40, 622 and 1056), a 4th degree polynomial (5 alignment points at positions 40, 331, 622, 809 and 1056) or a 5th degree polynomial (10 or 20 alignment points equidistantly spaced across the window). From FIG. 4B, it is clear that fitting to even a low degree polynomial (2nd degree) confers a significant and appropriate correction for the run time distortion. For example, the deviation from the average run time of all the aligned traces from this gel did not exceed 60 sec, which is equivalent to approximately 4 nt. This deviation is even smaller with the 4th degree polynomial, and is less than 1 nt when the 5th degree polynomial was used for linearization and alignment. Increasing the number of calibrant peaks used for alignment from 10 to 20 did not noticeably change the quality of the alignment.

The ability of a 2nd degree polynomial to provide adequate alignment, even though not able to fully linearize the data is indicative of the separability of the linearization and alignment processes. In considering the "smiling" effect across a gel which is illustrated in FIG. 4A, the run time as a function of DNA fragment size, $t_{iN}=f(N)$, may have a rather complicated function form, but this form does not change from lane i to lane j. Instead, the differences between lanes i and j can be characterized entirely in the scaling factors $C_i$ and $C_j$ to correct for stretch or shift. Thus, only these two parameters are necessary to compensate for the misalignment. The practical effect of this observation is to identify a subset of sequencing reactions which can be analyzed with lower order polynomials.

For example, when using shorter gels to analyze fewer bases, linearization of the traces is not as important as alignment. This is true for the MICROCEL™ 300 gel (11 cm length) which can be used for sequencing up to 450 nt. On such short gels, the deviation from linearity is frequently less than 15%, but misalignment can still be significant. Lower order polynomials with fewer calibration points may be used in this case. Thus, when sequencing targets of less than 500 nt, it may be sufficient to utilize a linear or 2nd order polynomial with only two or 3 calibrant peaks. This choice is determined by the experimentally observed interbase spacing, and whether the base number and a function of migration time may be approximated by a linear function.

The method of the invention is suitably practiced using an integrated apparatus which is programmed to collect sequencing and calibrant data traces, to linearize and align them in accordance with the invention, and then to call the base sequence of the target. Two specific apparatus which can be used for this purpose are described below. In discussing these apparatus, the term "integrated" does not require that all of the functions be performed by components disposed within a common housing. Thus, the electrophoretic separation and detection may take place in one component, referred to herein as the "electrophoresis unit", of the integrated apparatus which is connected to a second component, referred to herein as a "data analysis unit", which processes the data traces and provides an output of the called base sequence. This is particularly appropriate when a networked system is used in which one central data analysis unit is connected to multiple electrophoretic separation and detection units. (See U.S. Pat. No. 5,776,767). The connection between the electrophoretic unit and the data analysis unit may be a wired connection, a wireless connection such as an IR link, or it may be via a connection to a remote location. As used herein, the term "connection to a remote location" is intended to encompass connections achieved by modems and all forms of communication through distributed information transmission systems such as the Internet.

When using the method of the invention, in the embodiments discussed above each lane of the gel produces a calibrant data trace and one or more sequencing data traces. Alternatively, one could use a calibrant set in, for example, every other lane and use an adjacent lane or interpolate the values from two adjacent for lanes to arrive at calibration coefficients for the lane in which no calibrant fragment set was run. The selection of approach will depend in part of the type of gel used. For example, where the gel is continuous, the best results may be obtained using an interpolation of two adjacent lanes, since the lanes on each side of a given lane will provide information about variability of the intermediate lane. On the other hand, if spacers are used to divide the gel into smaller areas (for example glue divider lines separating each two lanes of a Visible Genetics Inc. MICROCEL cassette), then the best choice will frequently be the use of the adjacent lane between the same pair of divider lines.

In either case, whether calibrant fragment sets are used in every lane or in some useful portion of the lanes, the instrument used must be able to detect a number of labels equal to the number of samples run in the calibrant-containing lane plus one. Stated differently, one can run one sample per lane if the instrument is capable of detecting two label types, two samples per lane if the instrument is capable of detecting three label types, and so on. The art now contains examples of sequencers which can detect and distinguish between two or more label types, including for example those described in U.S. Pat. Nos. 5,213,673 and 5,171,534, and in those found in commercially available apparatus such as Visible Genetics Inc. LONG READ TOWER™ and CLIPPER™ sequencers, and any of these sequencers can be combined with a data analysis unit in accordance with the invention to produce an integrated sequencing apparatus in accordance with the invention. In general, the electrophoresis unit includes a holder for fixing a gel in place; a power supply and electrodes for applying a voltage across the gel, and a detection system for obtaining an intensity versus time data trace for each spectral channel in each lane.

Figure 5:
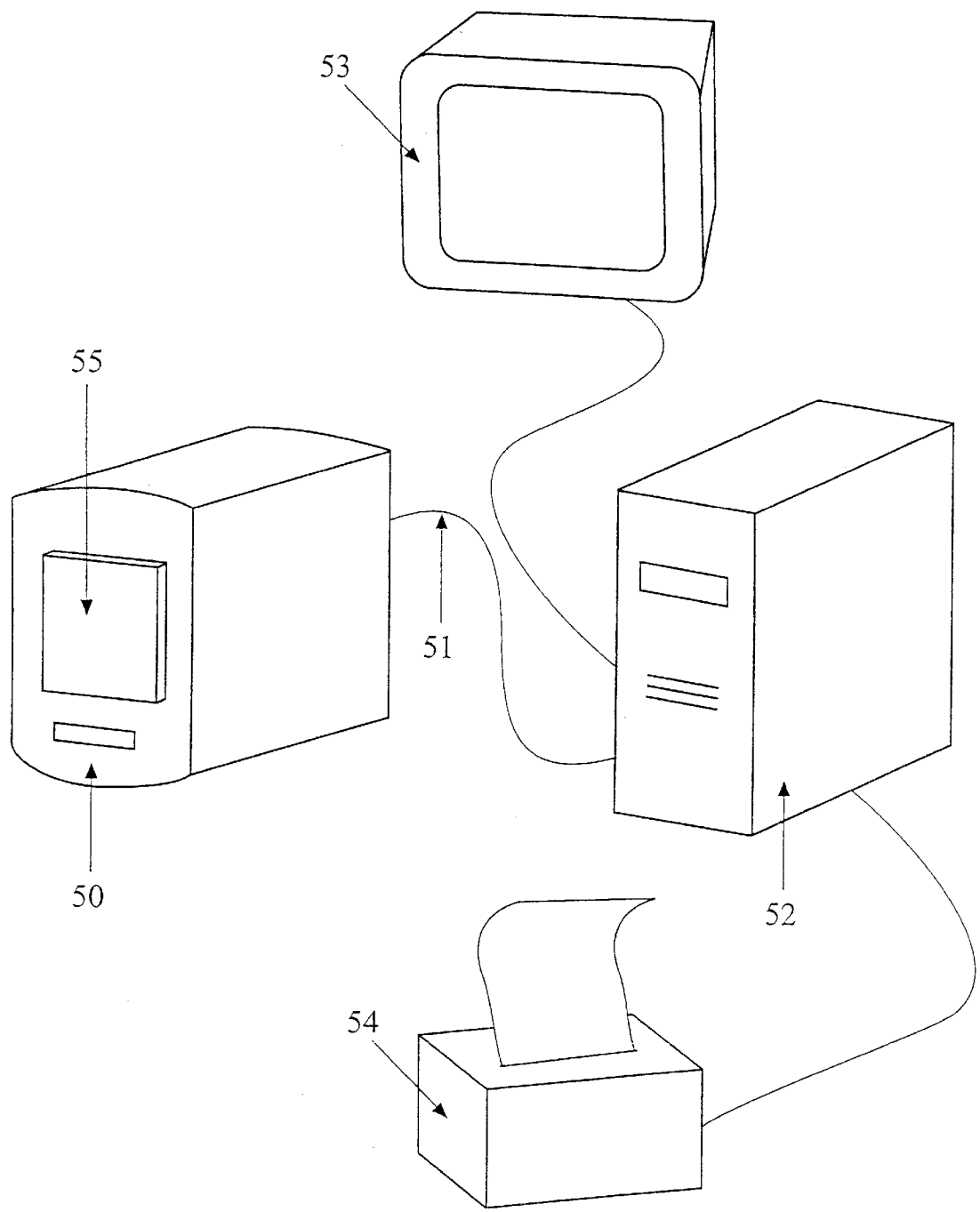
FIG. 5 shows an exterior view of an integrated DNA sequencing apparatus of the invention.

FIG. 5 shows an integrated apparatus of the invention. The electrophoresis unit 50 is connected via a wired connection 51 to a data analysis unit 52. The data analysis unit is in turn connected to one or more output devices such as display 53 and printer 54. Within the electrophoresis unit 50 is a detection system for detecting labeled polynucleotide fragments as they migrate in gel 55.

Figure 6:
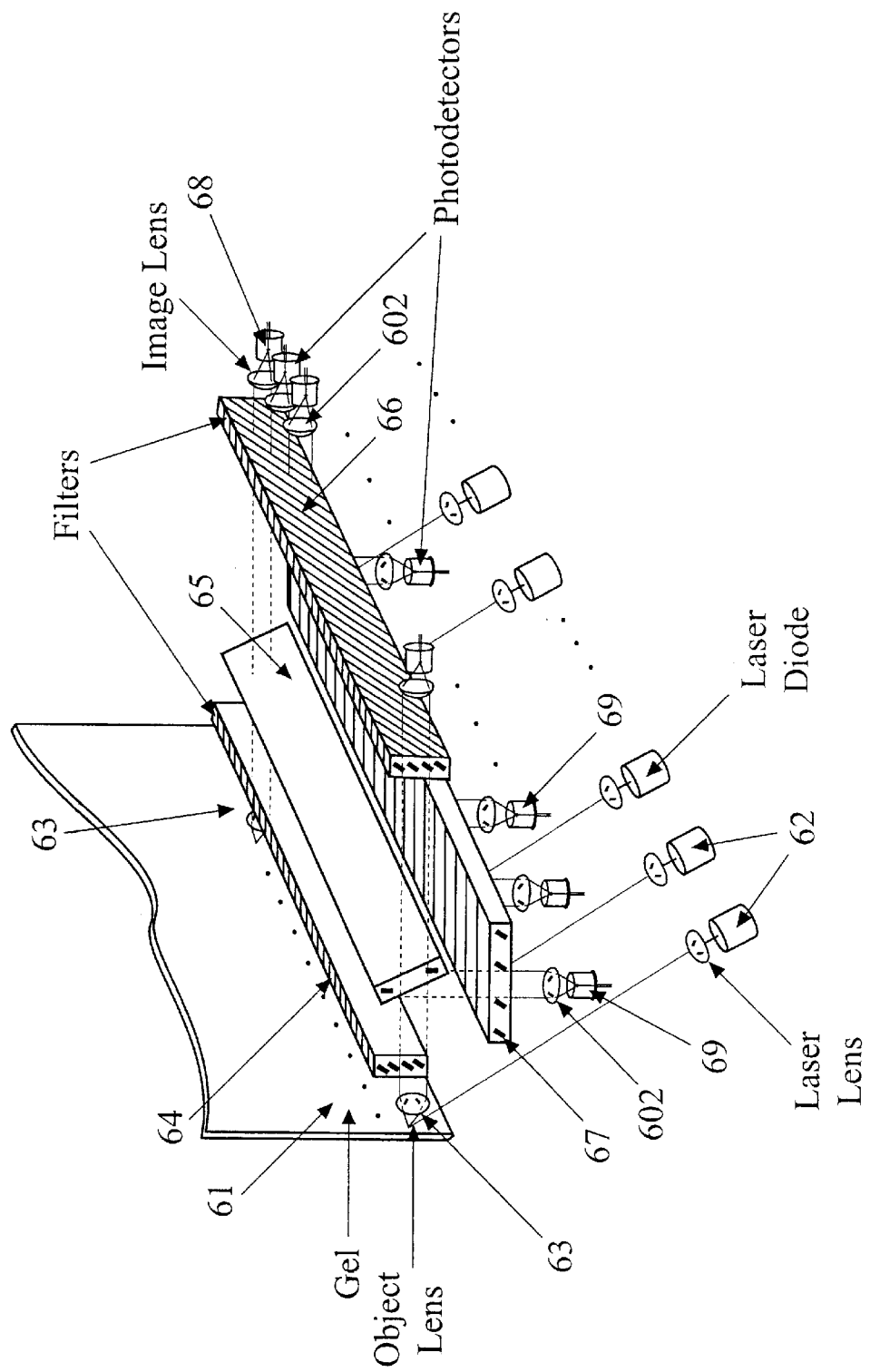
FIG. 6 shows an embodiment of a detection system useful for the detection of two labels.

FIG. 6 shows an embodiment of a detection system useful for the detection of two labels, and therefore useful in a method in which one sample fragment set and one calibrant fragment set are run in each lane. As shown, the gel 61 has a plurality of detection sites. Laser diodes 62 act as excitation sources to provide an excitation beam to each irradiation site. Lenses 63 (one per detection site) collect emitted light and pass it through a cut-off filter 64 (selected to exclude stray light and a portion of light from the excitation source) to a dichroic filter 65. The dichroic filter 65 substantially transmits light of the wavelength corresponding to the emission of one of the labels used in the gel and substantially reflects light of a wavelength corresponding to emission from the other of the labels used in the gel. Secondary bandpass filters 66, 67 are used to exclude from detectors 68, 69 light of incorrect wavelengths which may have been transmitted or reflected by the filters 66, 67. Filters 66, 67 also block transmission of light of the excitation wavelength to the detectors. Additional lenses 602 may be positioned between the secondary filters 66, 67 and the detectors 68, 69 to focus the emitted light on the detector. This type of detection system is found in the commercially available Visible Genetics CLIPPER and LONG READ TOWER™ sequencers.

Figure 7:
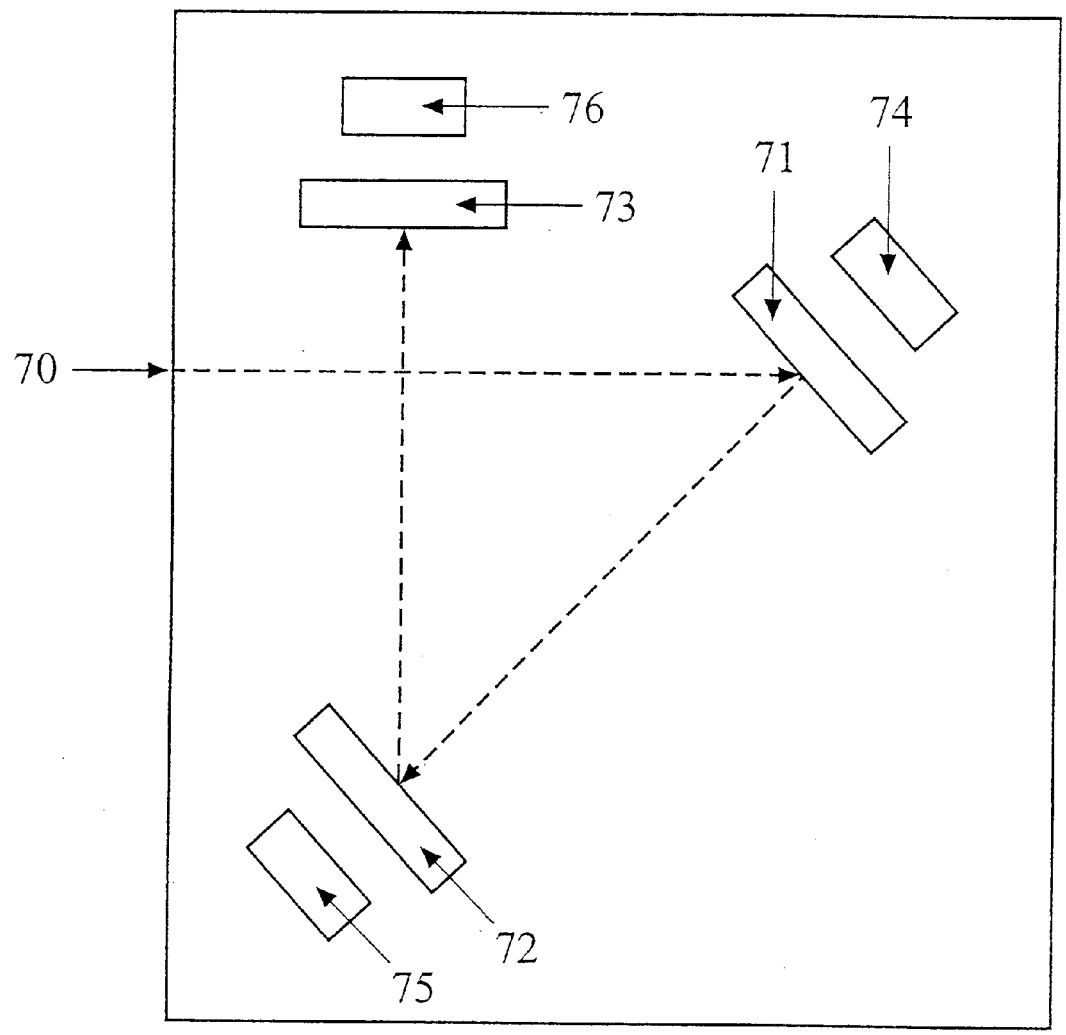
FIG. 7 shows an embodiment of a detection system useful for the detection of three labels.

FIG. 7 shows an embodiment of a detection system useful for the detection of three labels, and therefore useful in a method in which two sample fragments sets and one calibrant fragment set are run in each lane. The detection system assumes that all three labels can be excited with a single source and that the resulting transmitted (in the case of an absorption-based detection system) or emitted (in the case of a fluorescence based detection system) light are sufficiently different to be distinguished using bandpass filters, although additional light sources could be used if adequate signal cannot be obtained from three distinct labels with one irradiation source. The detection system comprises three filters and three detectors. Transmitted or emitted light 70 from the sample impinges on a first filter 71 which transmits light of a first wavelength, if present in the transmitted or emitted light 70, and reflects light of other wavelengths to impinge on filter 72. Filter 72, in turn, transmits light of a second wavelength, and reflects light of other wavelengths to impinge of filter 73. Filter 73 transmits only light of a third wavelength. The path of light between the successive filters is shown in FIG. 7 with a dashed line. Photodetectors 74, 75, 76 are disposed adjacent to the filters 71, 72, 73, respectively, to detect light which is transmitted by the filters. If labels associated with all three wavelengths are present in the sample, light will be transmitted by all three filters 71, 72, 73, producing a signal from all three photodetectors 74, 75, 76. If label associated with only the first and third wavelengths are present in the sample, then light will be transmitted by only the first and third filters, producing a signal from only two of the photodetectors. If label associated with only one of the wavelengths is present in the sample, only one filter will transmit light, producing signal from only one photodetector. Thus, by individually monitoring the signal from the three photodetectors, the configuration shown in FIG. 7 permits the evaluation of a sample containing up to three different labels in any combination, and does so without the use of moving parts or parts which require critical alignment.

When using the detection system of FIG. 7 in an integrated sequencing apparatus in accordance with the invention, one of the three wavelengths is assigned as the calibration wavelength and the other two are assigned as sample wavelengths. In general, the calibration wavelength will be detected the third detector 76 in the sequence, since this will have experienced the greatest attenuation of signal. Where there is a difference in quantum yield, it is best to assign the two most similar wavelengths to the sample lanes so that peaks sizes will be comparable.

Figure 8:
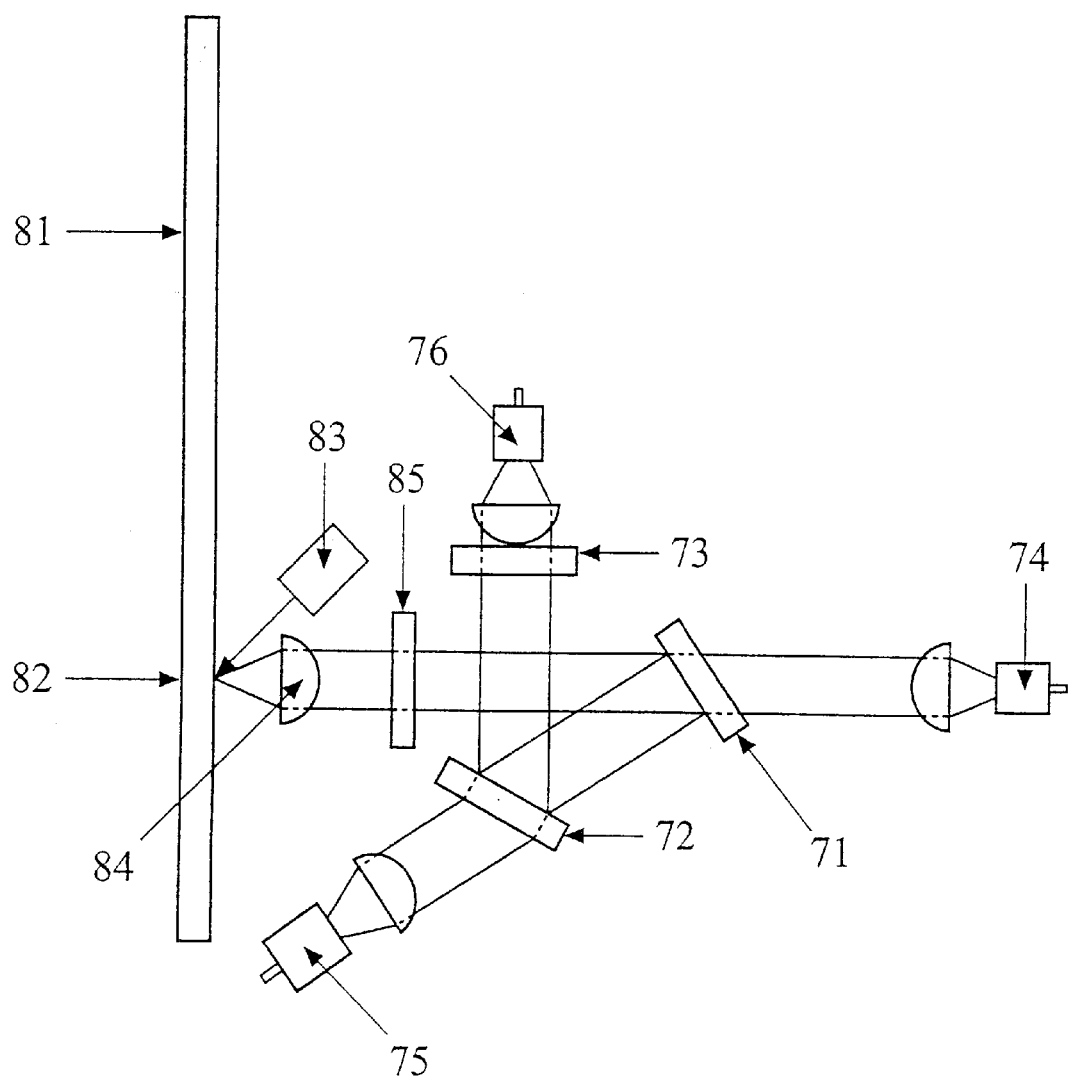
FIG. 8 shows a more detailed image of a detector module of the configuration shown in FIG. 7.

FIG. 8 shows a more detailed image of a detector module of the configuration shown in FIG. 7 in use to detect a sample migrating through detection zone 82 of an electrophoresis gel 81. A laser diode 83 is used to illuminate the detection zone 82 and stimulate fluorescent emission from any labels present within the zone. Light emitted from the detection zone is collected with objective lens 84. The objective lens collimates the collected light which propagates further in the detector module in the form of a parallel beam. Filter 85 is used to reject ambient light and stray light from the excitation laser which may be reflected toward the detector module. One filter 85 may be used for each detector module, or a common filter can be used for several detector modules. For example, in one embodiment of an integrated sequencing apparatus according to the invention, the glass filter 85 is common to 16 lanes or channels of the electrophoresis gel.

Several types of optical filters may be used as the filter 85. For example, in the case of an excitation laser having a wavelength of 635 nm, a suitable filter 85 is made from colored glass (RG645). This filter preferably has an antireflective coating on both surfaces in order to reduce light losses at the glass-air interface. The filter 85 may also be a special interference filter having high transmission in a range which transmits the desired wavelengths and high attenuation at the laser wavelength, for example, for a wide-band blocking filter with high transmission at 640–820 nm. Such filters not only blocks light of the excitation wavelength with good efficiency (transmission coefficient $\sim 10^{-5}$), they also have a high attenuation ($\sim 10^{-5}$) in the region above 820 nm where glass fluoresces strongly. Thus, the filter can reduce or eliminate background due to the use of glass components in the system.

Filters 71, 72, 73 are band pass interference filters, having transmission bands selected to match the diagnostic wavelengths of a given sample. In the three filter configuration of FIGS. 7 and 8, the first filter 71 is placed at an angle of 22.5 degrees relative to the optical axis of the light coming from the sample. This causes reflection at an angle of 45 degrees. The filter 72 is placed at an angle of 22.5 degrees with respect to the light reflected from filter 71. The filters 71 and 72 do not have the absorbing layers typical of bandpass filters. This allows reflection of non-transmitted wavelengths without significant loss. Finally, filter 73 is a normal bandpass filter disposed at a zero degree angle of incidence. The selection of 22.5 degrees provides great convenience in the manufacture of the detector module, since all of the angles required are either 45 degrees or 90 degrees. However, it will be appreciated that other configurations and angles could be used to achieve comparable results. In general, the choice of angles needs to be sufficient to separate the incoming beam at each filter from the reflected beam in the relatively short space available (generally less than 1 inch). On the other hand, angles greater than about 25–30 degrees are generally to be avoided, since the edge of the spectral curve of transmission at greater angles will not be sharp enough, and the transmission coefficient in the transparency band will drop. In this case, spectral selectivity of the beam splitting system may not be sufficiently high, although this factor will be minimized by using labels with substantially different diagnostic wavelengths.

The required bandwidth for filters 71, 72 and 73 will depend on the degree of separation of the emissions from the labels being employed. In general, the bandwidth will be about 20–30, and more preferably about 20 nm. The transmission spectra of the three filters 71, 72, 73 are such that the transmitted light is also transmitted by the glass filter 85, and preferably such that there is no overlap between the bandpass of the filters. Some overlap of filter bandpass can be tolerated, however, if the order of the filters is selected such that substantially all light of a first diagnostic wavelength is transmitted through one filter and not reflected to a second filter with an overlapping bandpass. Correction factors might also be employed to subtract out light of the wrong diagnostic wavelength that might pass through certain filter combinations.

As noted above, a suitable combination of dyes for a three-dye system are the cyanine dyes known by the names CY5, CY 5.5 and CY7 (Amersham), with CY 7 being used as the calibrant label. These dyes can all be excited using a 638 nm laser diode to produce emitted light of different spectral characteristics, having maxima at 665, 705 and 775 nm, respectively. Three band pass interference filters can be used to isolate each of these wavelengths in turn. For example, bandpass filters are commercially available which transmit light at 660–680 nm, 685–713 nm and 730–770 nm respectively, and these can be used in the present invention with the CY5, CY5.5 and CY7 cyanine dyes. The spectral curves corresponding to the different channels are well defined and have a transmission of about 80–90%. The width of the transmission bands is 25 nm for the first channel (CY 5.0), 30 nm for the second channel (CY 5.5) and 40 nm for the third channel (CY7). This difference in spectral width is introduced to compensate for the difference in the excitation efficiency of the different dyes, that results from the offset of the absorption spectrum by about 25 nm. This allows the efficient use of only one laser excitation source per channel.

The detection systems of FIGS. 6–8 produce output signals from each detector indicative of detected intensity associated with each label type. This signal is processed with an A-to-D converter, which may be located within the electrophoresis unit or within the data analysis unit, and is them ready for linearization and alignment prior to base calling.

Figure 9:
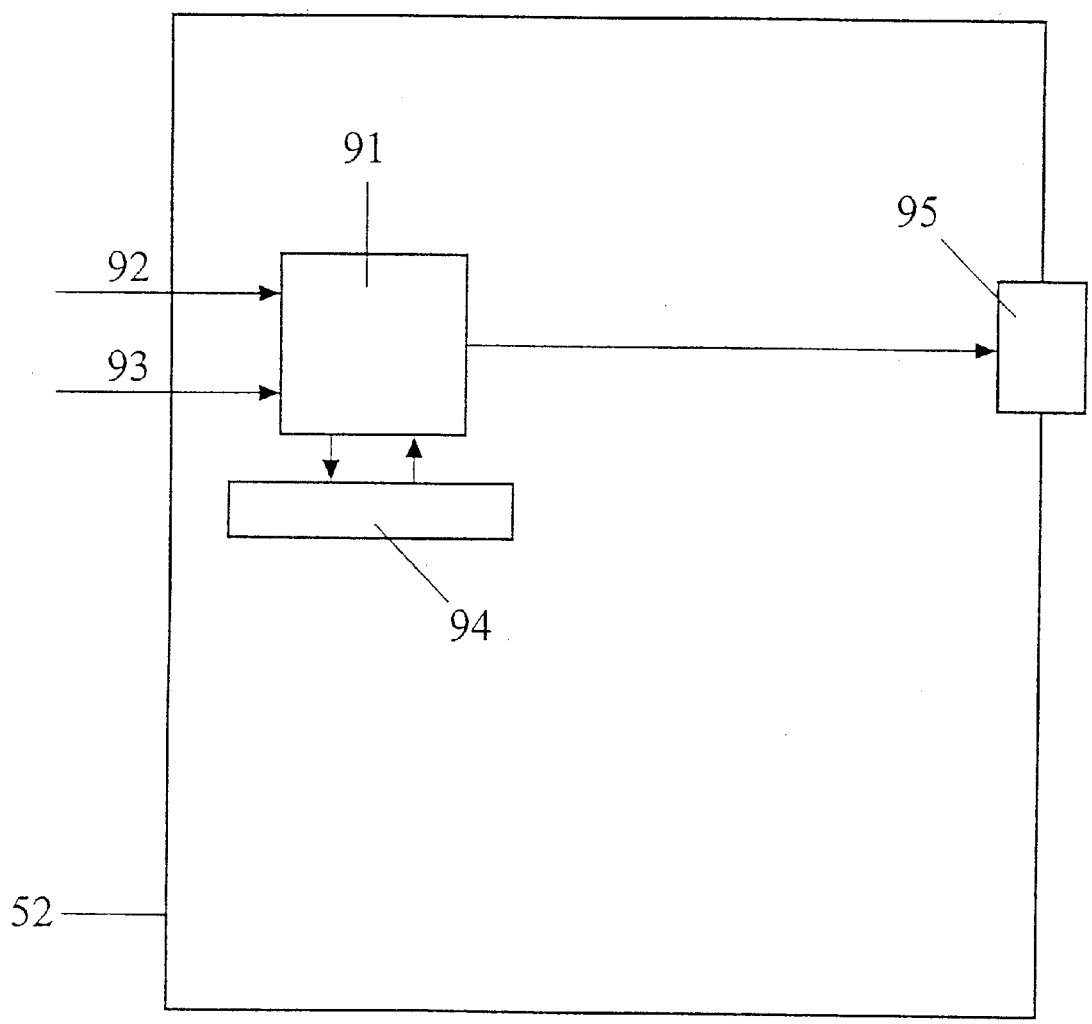
FIG. 9 shows a diagram of interior a data processing unit 52 for processing data received from an electrophoresis unit.

FIG. 9 shows a diagram of interior a data processing unit 52 for processing data received from an electrophoresis unit. As shown, processor 91 receives two input data streams 92, 93 per lane, reflecting the signals for the sequencing fragment set(s) and the calibrant fragment set, respectively. These raw data stream may be stored, for example on a disk drive 94 for later retrieval and processing by processor 91. The processor is also connected to one or more ports 95 which provide connection to output devices such as display 53 and printer 54.

Figure 10:
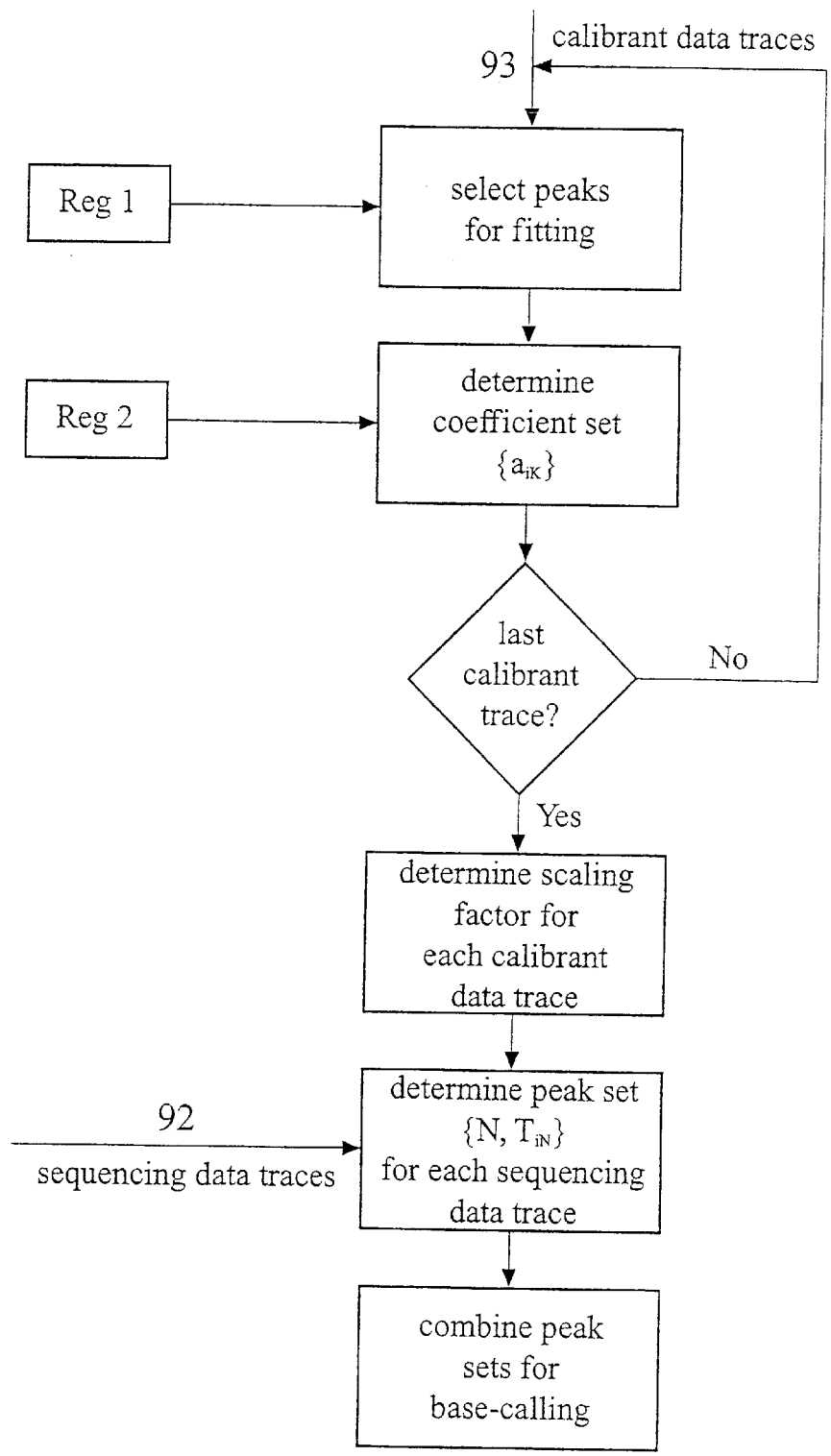
FIG. 10 shows a flow chart of the linearization and fitting procedure carried out by a data analysis unit in accordance with the invention.

FIG. 10 shows a flow chart of the linearization and fitting procedure carried out by the processor 91. The calibrant data trace 93 is first processed to select the peaks that will be used in the fitting process. As discussed in more detail below, in some case the calibrant polynucleotide fragment set may include fragments of only a limited number of sizes equal to the desired number of calibrant peaks. In this case, the selection process is trivial, in that all of the peaks are selected. In other cases, however, such as that employed in the preliminary tests of the invention using peaks from the M13 T track as the calibrant peaks, the calibrant data trace may include many more peaks than will be used in the calibration curve fitting. The selection of peaks is guided by an input from memory register Reg 1, which stores the number of peaks to be selected. The selected peaks are then used to determine a set of coefficient $\{a_{ik}\}$, where k, the order of the polynomial to be fit is a parameter provided from memory register Reg 2. These steps are then repeated for additional calibrant data traces from the electrophoresis gel until a set of coefficient has been generated for each of the calibrant data traces.

The next step is the determination of the scaling factor for each calibrant data trace. This scaling factor stretches or shrinks each of the data traces as necessary to have the corrected total run times of all of the calibrant data traces be the same. Thus, for example, if the first calibrant data trace is taken as a starting point and assigned a scaling factor of 1, the length of every other calibrant data trace is the ratio:

$$\frac{\text{actual run time for the first calibrant data trace}}{\text{actual run time of subsequent calibrant data trace}}$$

These numbers may be stored in volatile memory registers, or on a non-volatile storage medium such as disk 94.

The next step is the application of the coefficient sets and scaling factors to the sequencing data traces 92 to determine a peak set $\{N, T_{iN}\}$ for each of the sequencing data traces. As described above, this procedure entails calculating the real times $t_{iN}$ at which the Nth peak would be expected if the peaks were spaced at the intervals defined by the corrected time domain, and seeing if a peak exists at that location in the raw data trace. When a peak does exist, the peak is assigned the peak number N, and placed in the sequencing data table. When four bases are explicitly determined, the net result of this is four data sets, an A data set which is a list of the base position numbers at which an A base occurs, a C data set which is a list of the base position numbers at which a C base occurs, a G data set which is a list of the base position numbers at which a G base occurs, and a T data set which is a list of the base position numbers at which a T base occurs. These data sets are combined in base position number order to produce a combined data set which can be used directly for base calling.

It should be noted that where the identity of less than all of the bases are being explicitly determined (for example as described in U.S. Pat. No. 5,834,189), the method of the invention may not require the determination of the scaling coefficient $C_i$. This would be the case if the sequencing data traces from a lane were being considered individually, and not being combined with sequencing data traces from other lanes.

A final aspect of the invention to be addressed is the nature of the calibrant polynucleotide fragment set. As will be apparent from the foregoing discussion, one option is to use a set of fragments generated from a polynucleotide of known sequence and of the correct length for the calibrant polynucleotide fragment set, and then to select appropriately-spaced peaks for use in the fitting process. Within this option is the further option of using as the calibrant a standard polynucleotide of known sequence which is of the same type as the unknown sequence being targeted. The use of a naturally occurring sequence, with a mixture of base types, and in particular the use of the standard of the same type may be advantageous if the inherent base composition of the target has an effect on the migration rates of the fragments, because the migration of the experimental fragments and the calibrant fragments will be similarly effected. This type of fragment mixture is also desirable since it can be generated at the same time, and with the same chemistry as the experimental sequencing polynucleotide fragment sets, thus eliminating another potential source of differences between the calibrant and the experimental fragment. The use of fragment mixtures with extraneous fragments has the drawback, however, of increasing the cost since considerable labeled primer and termination reagent is utilized to fragments which are not required for the analysis. Accordingly, it may be desirable to utilize calibrant polynucleotide fragments sets which contain only the number of peaks actually desired, or only a few extra peaks.

Amersham Pharmacia Biotech (APB) markets size markers for use with the single-dye ALFEXPRESS™ and ALF™ sequencers. These markers are available as individual markers of various sizes (50, 100, 150, 200, 250 and 300 nt) or as mixtures of 10 fragments spanning the range from 50–500 nt or of 5 fragments spanning the range from 600–1600 nt. The fragments are labeled with CY5 or fluorescein (the dyes detected in the two sequencers) and, when used in accordance with the APB instructions, the markers and the experimental sequencing fragments have the same label and are run in separate lanes. Nevertheless, these fragments could be used in the method of the invention by selecting different labels for the sequencing fragments sets, or by obtaining comparable fragments with a different label (such as CY7). Such fragments can be made using PCR techniques and different labeled primers, or by chemical synthesis.

The invention will now be further described with reference to the following non-limiting examples.

EXAMPLE 1

Sequencing polynucleotide fragments sets (one for each base type) were generated by cycle sequencing of ultrapure M13mp18 single-stranded DNA template (Pharmacia #27-1546) using CY5 and CY5.5-labeled-20 universal primer and Thermosequenase (Amersham #E79000Z), and engineered mutant of Taq DNA polymerase which contains an F667Y substitution, and also an inactivation of the 5'->3'endonuclease domain. In cycle sequencing, this mutant produces bands of relatively uniform intensity. Van der Horn et al., *Biotechniques* 22: 758–765 (1997). A calibrant polynucleotide fragment set (ddT terminated only) was generated using the same methodology and a CY7-labeled primer. The dye-labeled primers were prepared by the phosphoramidite precursor method (Brush & Anderson, U.S. Pat. Nos. 5,556,959 and 5,808,044).

The sequencing polynucleotide fragment sets and the calibrant polynucleotide fragment set were analyzed on a two-color sequencer (Visible Genetics LONG READ TOWER™) and a prototype three-color instrument having an detector configuration of the type shown in FIG. 7. Both of these instruments achieve an electrophoretic separation of fluorescently-labeled DNA ladders on disposable, 50 µm thick MICROCEL™ cassettes. A separation length of 25 cm was used for all gels.

The MICROCEL™ cassettes were filled with 6% SUREFILL™ solution (nominally 5.5–6% acrylamide, 1×TBE, 6.5 M urea, plus crosslinker and initiator). The gels were polymerized by irradiating the MICROCEL™ with UV light (λmax=365 nm) for 3 minutes at an incident intensity of ~30 mW/cm². After polymerization, the gel-filled MICROCEL™ cassette was placed in the sequencer, and preheated to 60° C. prior to loading samples.

For the two-color sequencer, each sample consisted of a single ddA-, ddC, ddG- or ddT-terminated reaction labeled with one dye mixed with a calibrant labeled with a second dye. In the two dye system, either of the CY5 or the CY5.5 set could have been used as the experimental set in this test of the system, with the calibrant being labeled with one of the other two dyes. For the three-color sequencer, two different dideoxy-terminated reactions, labeled with CY5 and CY5.5 dyes, respectively, are mixed with a CY7-labeled calibrant. The three co,.or instrument has lower sensitivity to CY7 dye, because it is difficult to equalize excitation conditions for all three dyes simultaneously without using multiple excitation sources, and because the filter sets have been chosen to optimize the excitation efficiencies for the CY5 and the CY5.5 dyes. For this reason, it is best to use the CY7 dye as the calibrant label and not as a sequencing label.

Once loading is finished, a high voltage is applied to the gel from a built-in stabilized power supply. Typically, a voltage of 2500–2800 V is dropped over an inter-electrode distance of 28 cm. Bands of labeled polynucleotide are detected in real time at a detection point 25 cm from the loading point. Data sampling was performed at intervals of 0.5 seconds. This corresponds to 8–15 data points per electrophoretic peak and results in ~21,600 data points per spectral channel being collected over the course of a typical 3 hour run. The raw data from each gel lane (fluorescence intensity in 2 or 3 spectral channels, as a function of time) is corrected for cross-talk between the spectral channels and saved for later analysis.

The data traces were generally well aligned as judged by visual inspection. As a result, base calling of the data traces directly without prior linearization using GENE OBJECTS™ v. 3.1 automated base calling software (Visible Genetics Inc) achieved a base call of 900 nt with an accuracy of 97%. When the data was linearized using a 5th order polynomial and 10 calibration peaks as described above, however, the read length at the same 97% accuracy increased to 1000 nt, a 10% improvement. Alternatively, for a 900 nt read-length, the accuracy improved from 97% to 98.5% when the data traces were first linearized and aligned in accordance with the invention.

EXAMPLE 2

Poorly aligned data traces are periodically obtained in experimental data. Typically these result from the use of a gel of poor quality, the formation of bubbles in the gel or temperature gradients. Temperature gradients may be characteristic of the sequencer or caused by variable properties across the gel. One such set of poorly aligned data traces was evaluated using the present invention. When base calling was attempted directly on these data traces using the GENE OBJECTS™ v 3.1 automated base calling software, it was possible to base call this run to only about 50 bases. In contrast, when the data was linearized using a 5th order polynomial and 10 calibration peaks as described above, a read length of 1000 nt at 97% accuracy was obtained.

What is claimed is:

1. A method for evaluation of a target DNA sequence comprising the steps of:

(a) preparing a first sample mixture comprising a first set of sequencing polynucleotide fragments having lengths indicative of the positions of a first type of base within the target DNA sequence, said first set of sequencing fragments being labeled with a first label, and a set of calibrant polynucleotide fragments having a plurality of known fragment lengths, said calibrant polynucleotide fragments being labeled with a calibrant label which is spectroscopically distinguishable from the first label;

(b) electrophoretically separating the polynucleotide fragments in the first sample mixture as a function of fragment length in a separation medium;

(c) detecting the first label and the calibrant label as they migrate in a common lane of the separation medium to produce a first sequencing data trace and a calibrant data trace;

(d) generating a calibrant data set having a specified number of elements, each element comprising a base position number and a migration time for a peak in the calibrant data set;

(e) fitting the calibrant data set to a polynomial having an order k to determine a first set of coefficients for linearization of a plot of migration time versus base position number, wherein k is an integer greater than 1, and the specified number of elements in the calibrant data set is at least equal to k+1;

(f) resampling the first sequencing data trace at time intervals corresponding to a standard peak spacing defined by the polynomial and the determined coefficients to detect peaks in the sequencing data trace; and (g) creating a first sequencing data set comprising a number of elements equal to the number of peaks detected by resampling of the sequencing data trace, each element comprising at least a base position number for the peak which is be determined from the polynomial and the determined coefficients, wherein the first sequencing data set indicates the positions of bases of the first type in the target DNA sequence.

2. The method of claim 1, wherein k is greater than or equal to 4.

3. The method of claim 1, wherein the number of elements in the calibrant data set is greater than 6.

4. The method of claim 3, wherein the number of elements in the calibrant data set is greater than or equal to 10.

5. The method of claim 4, wherein k is greater than or equal to 4.

6. The method of claim 1, further comprising the step of preparing one or more additional sample mixtures, wherein:

(i) each additional sample mixture comprises a first additional set of sequencing polynucleotide fragments having lengths indicative of the positions of an additional type of base within the target DNA sequence, wherein the additional type of base may be the same as or different from the first type of base;

(ii) the first additional set of sequencing fragments in each additional sampling mixture is labeled with a first additional label which may be the same as or different from the first label (iii) each additional sample mixture further comprises an additional set of calibrant polynucleotide fragments having a plurality of known fragments lengths, (iv) the additional set of calibrant polynucleotide fragments are labeled with an additional calibrant label which may be the same as or different from the first calibrant label and which is spectroscopically distinguishable from the first additional label in the same additional sample mixture;

(v) each additional sample mixture is loaded onto a separate lane of the same separation medium as the first sample mixture and electrophoretically separated concurrently with the first sample mixture and detected to produce an first additional sequencing data trace and an additional calibrant data trace;

(vi) an additional calibrant data set is generated from each additional calibrant data trace, and each additional calibrant data set is fitted to an additional polynomial having an order k to determine an additional set of coefficients for linearization of a plot of retention time versus base position number, wherein k is an integer greater than 1, and the specified number of elements in the additional calibrant data set is at least equal to k+1;

(vii) calibrant data trace-specific scaling factors are determined for each lane of the separation medium, said scaling factors being selected such that multiplication of the scaling factor and the total run time of the associated calibrant data trace results in a constant value across all lanes of the separation medium;

(viii) the first sequencing data trace is resampled at time intervals corresponding to a standard peak spacing defined by the polynomial and the determined coefficients multiplied by the associated scaling factor to detect peaks in the sequencing data trace;

(ix) additional sequencing data traces are resampled at time intervals corresponding to a standard peak spacing defined by the associated additional polynomial and the determined additional coefficients multiplied by the associated scaling factor to detect peaks in the additional sequencing data traces; and (x) creating additional sequencing data sets each comprising a number of elements equal to the number of peaks detected by resampling of an additional sequencing data trace, each element comprising at least a base position number for the peak which is determined from the associated additional polynomial and the determined additional coefficients.

7. The method of claim 6, wherein the first base an each additional base are different from one another, and wherein the first and additional sequencing fragment sets are different termination mixtures derived from the same source, further comprising the step of combining the first sequencing data set and the additional sequencing data sets to produce a combined sequencing data set that indicates the positions of bases of the first and additional types in the target DNA sequence.

8. The method of claim 1, wherein the first sample mixture further comprises a second set of sequencing polynucleotide fragments having lengths indicative of the positions of a second type of base within the target DNA sequence, said second set of sequencing fragments being labeled with a second label which is spectroscopically distinguishable from the first label and the calibrant label, and wherein (i) a second sequencing data trace is obtained by detection of the second label, (ii) the second sequencing data trace is resampled at time intervals corresponding to a standard peak spacing defined by the polynomial and the determined coefficients to detect peaks in the second sequencing data trace;

(iii) a second sequencing data set is created comprising a number of elements equal to the number of peaks detected by resampling of the second sequencing data trace, each element comprising at least a base position number for the peak which is be determined from the polynomial and the determined coefficients, wherein the second sequencing data set indicates the positions of bases of the second type in the target DNA sequence.

9. The method of claim 8, wherein the first sequencing fragment set and the second sequencing fragment set are different termination mixtures derived from the same source, further comprising the step of combining the first sequencing data set and the second sequencing data sets to produce a combined sequencing data set that indicates the positions of bases of the first and second types in the target DNA sequence.

10. The method of claim 9, further comprising the steps of preparing an additional sample mixture comprising first and second additional sets of sequencing polynucleotide fragments having lengths indicative of the positions of a first and second additional types of base within the target DNA sequence and an additional set of calibrant polynucleotide fragments having a plurality of known fragment lengths, wherein the first and second additional bases are different from each other and from the first and second types of bases whereby all four base types are represented and wherein the first and second additional sets of sequencing fragments and the additional set of calibrant fragments are each label with a first and second additional labels and an additional calibrant label, said labels being spectroscopically distinguishable from each other;

loading the additional sample mixture onto a lane of the same separation medium as the first sample mixture and separating the additional sample mixture concurrently with the first sample mixture;

obtaining first and second additional sequencing data traces and an additional calibrant data trace by detecting the first and second additional labels and the additional calibrant label as the fragments migrate through the separation medium;

generating an additional calibrant data set having a specified number of elements, each element comprising a base position number and a migration time for a peak in the calibrant data set;

fitting the additional calibrant data set to an additional polynomial having the order k to determine an additional set of coefficients for linearization of a plot of retention time versus base position number, wherein the specified number of elements in the additional calibrant data set is the same as in the first calibrant data set;

determining a scaling factor for the additional polynomial, said scaling factor being selected to equalize the total run time of the first calibrant data trace and the additional calibrant data trace;

resampling the first and second additional sequencing data traces at time intervals corresponding to a standard peak spacing defined by the additional polynomial and the determined coefficients, multiplied by the scaling factor, to detect peaks in the first and second additional sequencing data traces;

creating first and second additional sequencing data sets, each comprising a number of elements equal to the number of peaks detected by resampling of the first or second additional sequencing data trace, respectively, each element comprising at least a base position number for the peak which is be determined from the polynomial and the determined coefficients, multiplied by the scaling factor, wherein the first additional sequencing data set indicates the positions of bases of the first additional type in the target DNA sequence and the second additional sequencing data set indicates the positions of bases of the second additional type in the target DNA sequence;

combining the first and second additional data sets with the combined data set to produce a complete combined data set that indicates the positions of all four types of bases in the target DNA sequence.

11. A data analysis unit for use in analysis of DNA sequence data obtained using an electrophoresis unit, said DNA sequence data including at least one sequencing data trace and one calibrant data trace per lane, said data analysis unit comprising, (a) an input means for receiving the DNA sequence data;

(b) a processor for processing the DNA sequence data to produce a linearized and aligned data set; and (c) an output connector for communicating the linearized and aligned data set to a user;

wherein the processor is programmed to perform the steps of:

selecting peaks from each calibrant data trace for fitting;

fitting the selected peaks to a polynomial function to determine a coefficient set for each calibrant data trace effective to linearize a plot of peak number versus migration time;

determining a scaling factor for each calibrant data trace, said scaling factors being selected such that they normalize the total run time of the calibrant data traces to a common value;

applying the polynomial with the determined coefficients and the scaling factor for each calibrant to the sequencing data trace(s) from the same lane to generate a peak set $\{N, T_{iN}\}$ in a corrected time domain; and when the DNA sequence data includes two or more related sequencing data traces, combining the peak sets generated for the related data traces into a combined peak set for base calling.

12. An integrated apparatus for sequencing of nucleic acids comprising:

(a) an electrophoresis unit; and (b) a data analysis unit in accordance with claim 11.

13. The apparatus of claim 12, further comprising at least one output device.

14. The apparatus of claim 13, wherein the output device is a display.

15. The apparatus of claim 13, wherein the output device is a printer.

16. The apparatus according to claim 12, wherein the electrophoresis unit comprises a detector system effective to detect three different spectroscopically distinguishable labels per lane.

17. The apparatus of claim 16, wherein the detector system comprises a detector module for detection of light transmitted by or emitted from a sample, wherein the light, depending on the nature of the sample, may include light of up to three spectroscopically-distinguishable wavelengths, and wherein the detector module comprises:

three optical bandpass filters, one for each spectroscopically-distinguishable wavelength, each of said bandpass filters transmitting light of one of the spectroscopically-distinguishable wavelengths and reflecting light of other spectroscopically-distinguishable wavelengths; and three photodetectors, wherein the bandpass filters are disposed in an arrangement such that light which is not transmitted by a bandpass filter is reflected to impinge on a successive bandpass filter in the arrangement, and wherein each of the photodetectors is disposed to detect light which has been transmitted by a different one of the bandpass filters.

18. The apparatus according to claim 17, wherein the three bandpass filters transmit light of 660–680 nm, 685–715 nm and 730–770 nm, respectively.

* * * * *